(12) United States Patent
Rogers

(10) Patent No.: US 11,191,803 B2
(45) Date of Patent: Dec. 7, 2021

(54) LAMININ RECEPTOR PEPTIDES FOR THERAPY

(71) Applicant: Arpi Rogers, London (GB)

(72) Inventor: Arpi Rogers, London (GB)

( * ) Notice: Subject to any disclaimer, the term of this patent is extended or adjusted under 35 U.S.C. 154(b) by 0 days.

(21) Appl. No.: 16/477,092

(22) PCT Filed: Jan. 12, 2018

(86) PCT No.: PCT/GB2018/050078
§ 371 (c)(1),
(2) Date: Jul. 10, 2019

(87) PCT Pub. No.: WO2018/130839
PCT Pub. Date: Jul. 19, 2018

(65) Prior Publication Data
US 2019/0343915 A1 Nov. 14, 2019

(30) Foreign Application Priority Data

Jan. 12, 2017 (GB) .................. 1700529

(51) Int. Cl.
| | |
|---|---|
| *A61K 38/10* | (2006.01) |
| *A61K 38/17* | (2006.01) |
| *C07K 7/08* | (2006.01) |
| *C07K 14/00* | (2006.01) |
| *C07K 14/47* | (2006.01) |
| *A61P 21/00* | (2006.01) |
| *A61P 25/28* | (2006.01) |

(52) U.S. Cl.
CPC ............ *A61K 38/10* (2013.01); *A61K 38/177* (2013.01); *A61P 21/00* (2018.01); *A61P 25/28* (2018.01); *C07K 7/08* (2013.01); *C07K 14/00* (2013.01); *C07K 14/4748* (2013.01)

(58) Field of Classification Search
CPC ...... A61K 38/10; A61K 38/177; A61K 38/16; C07K 14/4748; C07K 14/00; C07K 7/08; C07K 2319/00; C07K 14/705; A61P 21/00; A61P 25/28
See application file for complete search history.

(56) References Cited

U.S. PATENT DOCUMENTS

| | | |
|---|---|---|
| 2002/0040001 A1 | 4/2002 | Weiss |
| 2004/0214272 A1 | 10/2004 | La Rosa |
| 2005/0288231 A1 | 12/2005 | Liesi |
| 2007/0041977 A1 | 2/2007 | Knackmuss |

FOREIGN PATENT DOCUMENTS

| | | |
|---|---|---|
| WO | 2005035580 | 4/2005 |
| WO | 2017077516 | 5/2017 |

OTHER PUBLICATIONS

Devos et al. Ligand-independent dimerization of the extracellular domain of the leptin receptor and determination of the stoichiometry of leptin binding. J Biol Chem. Jul. 18, 1997;272(29):18304-10. doi: 10.1074/jbc.272.29.18304.*
Zhou et al. Exploration of a N-terminal disulfide bridge to improve the thermostability of a GH11 xylanase from Aspergillus niger. J Gen Appl Microbiol. 2016;62(2):83-9. doi: 10.2323/jgam.62.83.*
Bensimon G, et al., "A Controlled Trial of Riluzole In Amyotrophic Lateral Sclerosis," New England Journal of Medicine, Mar. 3, 1994, pp. 585-591, vol. 330, No. 9.
International Search Report and Written Opinion of PCT/GB2018/050078, dated Mar. 22, 2018.

* cited by examiner

*Primary Examiner* — Gregory S Emch
(74) *Attorney, Agent, or Firm* — Quarles & Brady LLP

(57) ABSTRACT

The present invention relates, to a laminin receptor peptide for use in the treatment of amyotrophic lateral sclerosis (ALS), which is also known as Motor Neurone Disease (MND) and can include Frontotemporal Dementia (FTD). The invention also encompasses the laminin receptor peptide, nucleic acids encoding the laminin receptor peptide, vectors comprising the nucleic acids and compositions comprising the laminin receptor peptide.

15 Claims, No Drawings
Specification includes a Sequence Listing.

```
                     SEQUENCE LISTING

<160> NUMBER OF SEQ ID NOS: 7

<210> SEQ ID NO 1
<211> LENGTH: 15
<212> TYPE: PRT
<213> ORGANISM: Artificial
<220> FEATURE:
<223> OTHER INFORMATION: Peptide

<400> SEQUENCE: 1

Val Pro Ser Val Pro Ile Gln Gln Phe Pro Thr Glu Asp Trp Ser
1               5                   10                  15

<210> SEQ ID NO 2
<211> LENGTH: 16
<212> TYPE: PRT
<213> ORGANISM: Artificial
<220> FEATURE:
<223> OTHER INFORMATION: Peptide

<400> SEQUENCE: 2

Cys Val Pro Ser Val Pro Ile Gln Gln Phe Pro Thr Glu Asp Trp Ser
1               5                   10                  15

<210> SEQ ID NO 3
<211> LENGTH: 32
<212> TYPE: PRT
<213> ORGANISM: Artificial
<220> FEATURE:
<223> OTHER INFORMATION: Peptide

<400> SEQUENCE: 3

Cys Val Pro Ser Val Pro Ile Gln Gln Phe Pro Thr Glu Asp Trp Ser
1               5                   10                  15

Cys Val Pro Ser Val Pro Ile Gln Gln Phe Pro Thr Glu Asp Trp Ser
                20                  25                  30

<210> SEQ ID NO 4
<211> LENGTH: 45
<212> TYPE: DNA
<213> ORGANISM: Artificial
<220> FEATURE:
<223> OTHER INFORMATION: Peptide

<400> SEQUENCE: 4
gtgcccagcg tgcccatcca gcagttcccc accgaggact ggagc          45

<210> SEQ ID NO 5
<211> LENGTH: 48
```

```
<212> TYPE: DNA
<213> ORGANISM: Artificial
<220> FEATURE:
<223> OTHER INFORMATION: Peptide

<400> SEQUENCE: 5
tgcgtgccca gcgtgcccat ccagcagttc cccaccgagg actggagc                    48

<210> SEQ ID NO 6
<211> LENGTH: 295
<212> TYPE: PRT
<213> ORGANISM: Homo sapiens

<400> SEQUENCE: 6
```

Met Ser Gly Ala Leu Asp Val Leu Gln Met Lys Glu Glu Asp Val Leu
1               5                   10                  15

Lys Phe Leu Ala Ala Gly Thr His Leu Gly Gly Thr Asn Leu Asp Phe
            20                  25                  30

Gln Met Glu Gln Tyr Ile Tyr Lys Arg Lys Ser Asp Gly Ile Tyr Ile
        35                  40                  45

Ile Asn Leu Lys Arg Thr Trp Glu Lys Leu Leu Leu Ala Ala Arg Ala
    50                  55                  60

Ile Val Ala Ile Glu Asn Pro Ala Asp Val Ser Val Ile Ser Ser Arg
65                  70                  75                  80

Asn Thr Gly Gln Arg Ala Val Leu Lys Phe Ala Ala Ala Thr Gly Ala
                85                  90                  95

Thr Pro Ile Ala Gly Arg Phe Thr Pro Gly Thr Phe Thr Asn Gln Ile
            100                 105                 110

Gln Ala Ala Phe Arg Glu Pro Arg Leu Leu Val Val Thr Asp Pro Arg
        115                 120                 125

Ala Asp His Gln Pro Leu Thr Glu Ala Ser Tyr Val Asn Leu Pro Thr
    130                 135                 140

Ile Ala Leu Cys Asn Thr Asp Ser Pro Leu Arg Tyr Val Asp Ile Ala
145                 150                 155                 160

Ile Pro Cys Asn Asn Lys Gly Ala His Ser Val Gly Leu Met Trp Trp
                165                 170                 175

Met Leu Ala Arg Glu Val Leu Arg Met Arg Gly Thr Ile Ser Arg Glu
            180                 185                 190

His Pro Trp Glu Val Met Pro Asp Leu Tyr Phe Tyr Arg Asp Pro Glu
        195                 200                 205

Glu Ile Glu Lys Glu Glu Gln Ala Ala Ala Glu Lys Ala Val Thr Lys
    210                 215                 220

Glu Glu Phe Gln Gly Glu Trp Thr Ala Pro Ala Pro Glu Phe Thr Ala
225                 230                 235                 240

Thr Gln Pro Glu Val Ala Asp Trp Ser Glu Gly Val Gln Val Pro Ser
                245                 250                 255

Val Pro Ile Gln Gln Phe Pro Thr Glu Asp Trp Ser Ala Gln Pro Ala
            260                 265                 270

Thr Glu Asp Trp Ser Ala Ala Pro Thr Ala Gln Ala Thr Glu Trp Val
        275                 280                 285

Gly Ala Thr Thr Asp Trp Ser
    290                 295

```
<210> SEQ ID NO 7
<211> LENGTH: 885
<212> TYPE: DNA
<213> ORGANISM: Homo sapiens
```

```
<400> SEQUENCE: 7
atgagcggcg ccctggacgt gctgcagatg aaggaggagg acgtgctgaa gttcctggcc          60
gccggcaccc acctgggcgg caccaacctg gacttccaga tggagcagta catctacaag         120
aggaagagcg acggcatcta catcatcaac ctgaaggaga cctgggagaa gctgctgctg         180
gccgccaggg ccatcgtggc catcgagaac cccgccgacg tgagcgtgat cagcagcagg         240
aacaccggcc agagggccgt gctgaagttc gccgccgcca ccggcgccac ccccatcgcc         300
ggcaggttca cccccggcac cttcaccaac cagatccagg ccgccttcag ggagcccagg         360
ctgctggtgg tgaccgaccc cagggccgac caccagcccc tgaccgaggc cagctacgtg         420
aacctgccca ccatcgccct gtgcaacacc gacagccccc tgaggtacgt ggacatcgcc         480
atcccctgca caacaaggg cgcccacagc gtgggcctga tgtggtggat gctggccagg          540
gaggtgctga ggatgagggg caccatcagc agggagcacc cctgggaggt gatgcccgac         600
ctgtacttct acagggaccc cgaggagatc gagaaggagg agcaggccgc cgccgagaag         660
gccgtgacca aggaggagtt ccagggcgag tggaccgccc ccgcccccga gttcaccgcc         720
acccagcccg aggtggccga ctggagcgag ggcgtgcagg tgcccagcgt gcccatccag         780
cagttcccca ccgaggactg gagcgcccag cccgccaccg aggactggag cgccgccccc         840
accgcccagg ccaccgagtg ggtgggcgcc accaccgact ggagc                         885
```

LAMININ RECEPTOR PEPTIDES FOR THERAPY

CROSS-REFERENCE TO RELATED APPLICATIONS

This application is the U.S. National Stage under 35 U.S.C. § 371 of International Application No. PCT/GB2018/050078, filed on Jan. 12, 2018, which claims the benefit of priority of Great Britain Patent Application No. 1700529.9, filed on Jan. 12, 2017, the content of which is incorporated herein by reference in its entirety.

FIELD OF THE INVENTION

The present invention relates, in general, to a laminin receptor peptide for use in the treatment of amyotrophic lateral sclerosis (ALS), which is also known as Motor Neurone Disease (MND) and can include Frontotemporal Dementia (FTD). The invention also encompasses the laminin receptor peptide, nucleic acids encoding the laminin receptor peptide, vectors comprising the nucleic acids and compositions comprising the laminin receptor peptide.

BACKGROUND TO THE INVENTION

Amyotrophic lateral sclerosis (ALS), which is also known as Motor Neurone Disease (MND) is an adult onset paralytic disease and can include Frontotemporal Dementia (FTD). The disease is characterised by initial muscle weakness at a focal point, which rapidly progresses to other regions of the body. Progressive paralysis continues to spread throughout the body leading to death by respiratory failure within 2-5 years. The majority of ALS/MND cases are considered to be sporadic, whilst 5-10% of cases are familial.

The severity of ALS/MND is measured using the ALS Functional Rating Scale Revised (ALSFRS-R). This is a twelve item test performed by means of a clinical interview or self-complete questionnaire. For each item, the patient receives a score between 4 (normal function) and 0 (severe disability) which are added to produce a total score out of 48. The lower the score the more severe the disease, with patients generally dying through suffocation when the score reaches about 12.

To date, no disease modifying therapy has been identified which is capable of delaying or preventing the rapid progress of ALS/MND. Riluzole is the only treatment currently licensed by the FDA for the treatment of this debilitating disease. Riluzole, a sodium channel inhibitor, preferentially blocks TTX-sensitive sodium channels, which are associated with damaged neurons. Riluzole has been shown to provide patients with only a 2-3 month survival advantage (Bensimon et al., N. Engl. J. Med. 1994, 330: 585-591). Edaravone, a free radical scavenger, has recently been approved for the treatment of ALS/MND in Japan. Edaravone failed to show efficacy during a 24 week treatment period in an initial Phase III trial (Abe et al., Amyotrophic Lateral Sclerosis and Frontotemporal Degeneration, 2014, 15: 610-617) but a second Phase III trial, performed on a selected mildly symptomatic group, demonstrated a loss of 5 points on the ALSFRS-R score over 24 weeks, compared to a placebo group who lost an average of 7.5 points during the same time period. Although this represents a slowing down of disease progression in this mildly symptomatic subgroup, Edaravone has not been demonstrated to be effective in patients having severe symptoms (characterised by a low ALSFRS-R score). There therefore exists a need for an effective treatment for ALS/MND, which can preferably be utilised by patients having both early stage and severe disease.

It is known in the art that elevated levels of plasma glucagon are found in ALS/MND patients (Hubbard et al., Neurology, 1992, 4:1532-1534). Since glucagon has catabolic and hypermetabolic effects (Charlton et al., Diabetes, 1998, 47: 1748-1756 & Preedy et al., Biochem J, 1985, 15: 575-581), hypermetabolism and muscle wastage are observed in ALS/MND patients and have been established as early indicators of ALS/MND (Doge et al., PNAS, 2013, 110:10812-10817). Furthermore, secretion of high levels of glucagon from pancreatic α-cells is accompanied by high levels of L-glutamate, co-secreted from the same glucagon containing α-cell granules (Hyashi et al. J Biol Chem., 278, 1966-1974). Secreted glutamate acts as a positive autocrine signal for further glucagon release, perpetuating the cycle of high glucagon and glutamate (Cabrera et al. Cell Metab. 2008, 7, 545-554). Consequently, plasma L-glutamate levels which are 3 to 5-fold higher than normal have been reported in ALS/MND patients, and are known to be excitotoxic (Blin et al., Rev. Neurol (Paris), 1991, 147, 392-394), Iwasaki et al. J Neurol Sci. 1992, 107, 219-222).

An inverse correlation between circulating levels of glucagon and the ALSFRS-R rating scale has been demonstrated in ALS/MND patients (Ngo et al., Journal of the Neurological Sciences, 2015, 357: 22-27.37), which is indicative of a role for raised glucagon levels in the pathogenesis of ALS/MND. The inventor hypothesises that a therapeutic treatment which reduces the levels of circulating glucagon could reduce ALS/MND symptoms, as measured by the ALSFRS-R score.

SUMMARY OF THE INVENTION

The inventor has surprisingly discovered that the addition of a laminin receptor peptide to isolated pancreatic islet cultures can significantly reduce the levels of secreted glucagon. The inventor has also surprisingly discovered that administration of a laminin receptor peptide can significantly reduce the progression of ALS/MND symptoms, as measured by the ALSFRS-R score.

Laminins are a family of signalling proteins within the extracellular matrix (ECM) which exert their signalling effects through their interaction with laminin receptors in cell membrane lipid rafts (MLRs). A variety of cell signalling proteins have been shown to partition into membrane lipid rafts and it is thought that these lipid rafts enable signalling molecules and their receptors to interact in order to permit signalling. The proper organisation of membrane lipid rafts is therefore essential for productive transmission of signals within the ECM, permitting neuronal communications and muscular responses. Without wishing to be bound by theory, the inventor hypothesises that the high levels of circulating glucagon observed in ALS/MND patients disrupt the lipid raft organisation, preventing effective signalling within the ECM. Coupled with muscle wastage caused by the hypermetabolic effects of glucagon, the lipid raft disruption prevents appropriate neural signals reaching patients' muscles, worsening ALS/MND symptoms. The administration of a laminin receptor peptide to patients with ALS/MND appears to repair the lipid raft structure, restoring signalling within the ECM and leading to a reduction in ALS/MND symptoms.

In a first aspect the invention provides a laminin receptor peptide for use in a method of treating amyotrophic lateral sclerosis (ALS), Motor Neurone Disease (MND) or Frontotemporal Dementia (FTD), which is hypothesised to function by reducing pancreatic secretion of glucagon.

In a second aspect the invention provides a peptide comprising an amino acid sequence having sequence identity to the peptide of SEQ ID NO: 1. For example, the peptide may have 70%, 80%, 90%, 95% or more sequence identity to the peptide of SEQ ID NO: 1. Preferably the peptide comprises or consists of the sequence of SEQ ID NO: 1. Also encompassed within this aspect of the invention is a peptide multimer comprising two or more peptide molecules, preferably linked by a disulphide bridge.

DETAILED DESCRIPTION OF THE INVENTION

The invention, in general, provides a laminin receptor peptide for use in the treatment of amyotrophic lateral sclerosis (ALS), which is also known as Motor Neurone Disease (MND) and can include Frontotemporal Dementia (FTD), which is thought to occur through reduction of glucagon levels. The invention also provides the laminin receptor peptide, nucleic acids encoding the laminin receptor peptide, vectors comprising the nucleic acids and compositions comprising the laminin receptor peptide.

The inventor has surprisingly discovered that administration of the laminin receptor peptide described herein to patients with ALS/MND leads to a reduction in ALS/MND symptoms, preferably measured using the ALSFRS-R score. This improvement in symptoms is thought to result from repair of the lipid raft structures in cell membranes and signalling connectivity within the ECM which has been disrupted in ALS/MND patients by high circulating glucagon levels.

Treatment of ALS/MND

In a first aspect the invention provides a laminin receptor peptide for use in a method of treating amyotrophic lateral sclerosis (ALS), Motor Neurone Disease (MND) or Frontotemporal Dementia (FTD).

Within this aspect, a method of treating amyotrophic lateral sclerosis (ALS), Motor Neurone Disease (MND) or Frontotemporal Dementia (FTD) by administering a laminin receptor peptide, and use of a laminin receptor peptide in the manufacture of a medicament for the treatment of amyotrophic lateral sclerosis (ALS), Motor Neurone Disease (MND) or Frontotemporal Dementia (FTD) are both contemplated. All embodiments discussed below in relation to the first aspect of the invention are also contemplated in relation to this method of treatment and medical use.

Laminin Receptor Peptide for the Treatment of ALS/MND

The laminin receptor peptide for use in a method of treating amyotrophic lateral sclerosis (ALS), Motor Neurone Disease (MND) or Frontotemporal Dementia (FTD) comprises a sequence derived from a laminin receptor. Preferably the laminin receptor is a human laminin receptor, such as the human laminin receptor having the amino acid sequence of SEQ ID NO: 6.

The laminin receptor is a type II transmembrane protein which is located within the lipid raft region of the plasma membrane (Jovanovic et al., Expert Opin. Ther. Patents, 2015, 25(5):567-582).

The sequence of the human laminin receptor is depicted in SEQ ID NO: 6. The amino-terminal portion of the receptor (amino acids 1-85) is located intracellularly, the central portion of the receptor (amino acids 86-101) forms the transmembrane domain and the carboxy-terminal portion of the receptor (amino acids 102-295) forms the extracellular domain (ECD). It is the extracellular domain of the laminin receptor which plays an important role in the structure of lipid rafts. Therefore, the laminin receptor peptide used for the treatment of amyotrophic lateral sclerosis (ALS), Motor Neurone Disease (MND) or Frontotemporal Dementia (FTD) within the present invention preferably comprises a sequence derived from the extracellular domain of the human laminin receptor, i.e. a sequence derived from amino acids 102-295 of SEQ ID NO: 6.

The inventor has surprisingly discovered that a peptide derived from the laminin receptor is particularly effective for the treatment of amyotrophic lateral sclerosis (ALS), Motor Neurone Disease (MND) or Frontotemporal Dementia (FTD). Therefore, in one embodiment the laminin receptor peptide for use in a method of treating amyotrophic lateral sclerosis (ALS), Motor Neurone Disease (MND) or Frontotemporal Dementia (FTD) according to the present invention comprises an amino acid sequence having sequence identity to the peptide of SEQ ID NO: 1. The inventor hypothesises that administration of this laminin receptor peptide can be used to treat amyotrophic lateral sclerosis (ALS), Motor Neurone Disease (MND) or Frontotemporal Dementia (FTD) because it repairs the lipid raft structure, restoring signalling within the extracellular martix. It is known that glucagon secretion from pancreatic α-cells is regulated by lipid rafts and disruption of lipid rafts by the cholesterol targeting drug methyl-β-cyclodextrin (MβCD) has been shown to reduce cholesterol by approximately 60% in a culture of a pancreatic α-cell line, resulting in a doubling of the glucagon secretion (Xia et al. Endocrinology 2007, 148, 2157-2167). In vivo studies have also shown that glucagon reduces the rate of transcription and translation of HMG-CoA (Ness et al., Proc. Soc. Exp. Biol. Med. 2000, 224, 8-19), reducing cellular cholesterol synthesis which is damaging to cholesterol-rich lipid rafts. Administration of a laminin receptor peptide comprising an amino acid sequence having sequence identity to the peptide of SEQ ID NO: 1 is hypothesised to reduce the progression of amyotrophic lateral sclerosis (ALS), Motor Neurone Disease (MND) or Frontotemporal Dementia (FTD) symptoms by repairing the lipid raft structure damaged by excessive glucagon secretion, restoring signalling within the extracellular matrix.

In certain embodiments, the laminin receptor peptide for use in a method of treating amyotrophic lateral sclerosis (ALS), Motor Neurone Disease (MND) or Frontotemporal Dementia (FTD) according to the present invention may comprise an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or more sequence identity to the peptide of SEQ ID NO: 1. Within these embodiments, sequence identity may be assessed by any means. However, sequence identity is preferably assessed using the Smith-Waterman algorithm.

Also contemplated within the present invention is a laminin receptor peptide for use in a method of treating amyotrophic lateral sclerosis (ALS), Motor Neurone Disease (MND) or Frontotemporal Dementia (FTD) according to the present invention wherein the laminin receptor peptide comprises a truncated version of any of the peptides contemplated above. For example, the laminin receptor peptide may comprise a peptide having 1, 2, 3, 4, 5, 6, 7, 8, 9, 10 or more amino acids truncated from the sequence of SEQ ID NO: 1 or a sequence having sequence identity thereto. Any truncations may occur at either the amino-terminus or the carboxy-terminus of SEQ ID NO: 1 or at both the amino-terminus and the carboxy-terminus of SEQ ID NO: 1.

In one embodiment, the laminin receptor peptide for use in a method of treating amyotrophic lateral sclerosis (ALS), Motor Neurone Disease (MND) or Frontotemporal Dementia (FTD) according to the present invention may comprise the amino acid sequence of SEQ ID NO: 1. Throughout the present application, the term "comprise", and variants thereof, is used in the open sense to indicate that the recited amino acid sequence is present but that additional amino acids may also be present within the peptide. Such additional amino acids, where present, may be present at the amino-terminus or the carboxy-terminus of the peptide or at both the amino-terminus and the carboxy-terminus of the peptide. In certain embodiments the laminin receptor peptide for use in a method of treating amyotrophic lateral sclerosis (ALS), Motor Neurone Disease (MND) or Frontotemporal Dementia (FTD) according to the present invention may not comprise any additional amino acids which form part of a contiguous sequence of amino acids found in the sequence of the laminin receptor (SEQ ID NO: 6) other than SEQ ID NO: 1.

In a further embodiment, the laminin receptor peptide for use in a method of treating amyotrophic lateral sclerosis (ALS), Motor Neurone Disease (MND) or Frontotemporal Dementia (FTD) according to the present invention may consist of the amino acid sequence of SEQ ID NO: 1. Throughout the present application, the term "consist", and variants thereof, is used in the closed sense to indicate that no additional amino acids are present within the peptide.

Any post-translational modification of the laminin receptor peptide for use in a method of treating amyotrophic lateral sclerosis (ALS), Motor Neurone Disease (MND) or Frontotemporal Dementia (FTD) according to the present invention is contemplated. For example, the peptide may be glycosylated, phosphorylated, acetylated or methylated at one or more amino acids.

Laminin Receptor Peptide Multimer for the Treatment of ALS/MND

In one embodiment, the laminin receptor peptide for use in a method of treating amyotrophic lateral sclerosis (ALS), Motor Neurone Disease (MND) or Frontotemporal Dementia (FTD) according to the present invention may be a peptide multimer comprising two or more laminin receptor peptide molecules. Herein, the terms "laminin receptor peptide molecule", "laminin receptor peptide", "peptide molecule" and "peptide" will be used interchangeably to refer to a laminin receptor peptide having any of the forms described above.

In one embodiment, the laminin receptor peptide multimer for use in a method of treating amyotrophic lateral sclerosis (ALS), Motor Neurone Disease (MND) or Frontotemporal Dementia (FTD) according to the present invention may comprise two, three, four, five, six, seven, eight, nine, ten or more laminin receptor peptide molecules. Preferably, the laminin receptor peptide multimer is a laminin receptor peptide dimer, i.e. comprises two laminin receptor peptide molecules.

In certain embodiments the two or more laminin receptor peptide molecules within the peptide multimer may or may not be identical. Preferably, the two or more laminin receptor peptide molecules within the peptide multimer each comprise or consist of the sequence of SEQ ID NO: 1.

The point of attachment between the two or more laminin receptor peptide molecules within the peptide multimer may be located at any position within the two or more laminin receptor peptide molecules. In certain embodiments the point of attachment may or may not be located at the same position within each laminin receptor peptide molecule. In certain embodiments the two or more laminin receptor peptide molecules may be attached through their termini. In a preferred embodiment in which the peptide multimer is a peptide dimer, the two laminin receptor peptide molecules are attached through their amino-termini.

Within the peptide multimer, two laminin receptor peptide molecules may be linked by a disulphide bridge. It is well known within the field of protein biochemistry that a disulphide bridge is formed by reaction between the thiol groups of two cysteine residues, and has the sequence R-S-S-R'. Within an embodiment in which the peptide multimer is a peptide dimer, the two laminin receptor peptide molecules may be attached in any orientation. Preferably the two laminin receptor peptide molecules are attached through their termini and more preferably the two laminin receptor peptide molecules are attached through their amino-termini. In other words, the disulphide bridge is preferably located at the amino-terminus of each laminin receptor peptide molecule.

It will be apparent to the skilled person that the peptide of SEQ ID NO: 1 does not include a cysteine residue required to form a disulphide bridge. Therefore, the invention contemplates the inclusion of an additional cysteine residue within each laminin receptor peptide molecule present within the peptide multimer. The additional cysteine residue may be located at any position within each laminin receptor peptide molecule and the additional cysteine residue may or may not be located at the same position within each laminin receptor peptide molecule. Preferably, the additional cysteine residue is located at either the amino-terminus or the carboxy-terminus of each laminin receptor peptide molecule. For example, all laminin receptor peptide molecules may have an additional cysteine residue located at their amino-terminus, all laminin receptor peptide molecules may have an additional cysteine residue located at their carboxy-terminus, or one or more laminin receptor peptide molecules may have an additional cysteine residue located at its amino-terminus and one or more laminin receptor peptide molecules may have an additional cysteine residue located at its carboxy-terminus. Preferably, the multimer is a dimer and both laminin receptor peptide molecules have an additional cysteine residue located at their amino-terminus.

Preferably the additional cysteine residue is present within each laminin receptor peptide molecule immediately adjacent to the sequence of SEQ ID NO: 1. However, the inclusions of additional amino acids (e.g. 1, 2, 3, 4, 5 or more additional amino acids) between the sequence of SEQ ID NO: 1 and the additional cysteine residue is also contemplated.

In a preferred embodiment, the laminin receptor peptide multimer for use in a method of treating amyotrophic lateral sclerosis (ALS), Motor Neurone Disease (MND) or Frontotemporal Dementia (FTD) according to the present invention is a peptide dimer. In a further preferred embodiment, the laminin receptor peptide dimer for use in a method of treating amyotrophic lateral sclerosis (ALS), Motor Neurone Disease (MND) or Frontotemporal Dementia (FTD) according to the present invention comprises the sequence of SEQ ID NO: 3. In a more preferred embodiment, the laminin receptor peptide dimer for use in a method of treating amyotrophic lateral sclerosis (ALS), Motor Neurone Disease (MND) or Frontotemporal Dementia (FTD) according to the present invention consists of the sequence of SEQ ID NO: 3.

In certain embodiments the laminin receptor peptide multimer for use in a method of treating amyotrophic lateral sclerosis (ALS), Motor Neurone Disease (MND) or Frontotemporal Dementia (FTD) according to the present invention may not comprise any additional amino acids which form part of a contiguous sequence of amino acids found in the sequence of the laminin receptor (SEQ ID NO: 6) other than SEQ ID NO: 1.

Treatment Protocols

Within this aspect of the invention, all treatment protocols are contemplated.

The patient to be treated within this aspect of the invention is preferably a human patient. However, the treatment of animal patients, and particularly non-human mammalian patients, is also contemplated. For example, the patient may be a dog, cat, cow, horse, llama, monkey or chimpanzee.

All methods of administration of the laminin receptor peptide for use in a method of treating amyotrophic lateral sclerosis (ALS), Motor Neurone Disease (MND) or Frontotemporal Dementia (FTD) are included within the scope of the invention. Preferably, the laminin receptor peptide is administrated intramuscularly, subcutaneously, intravenously, transmucosally, transdermally or orally.

Any dosage of the laminin receptor peptide for use in a method of treating amyotrophic lateral sclerosis (ALS), Motor Neurone Disease (MND) or Frontotemporal Dementia (FTD) is contemplated within the invention. However, the dose chosen preferably provides an improvement in ALS/MND symptoms in the patient. Preferably the improvement is measured as an improvement or a slowed decline in ALSFRS-R score relative to predicted decline.

Laminin Receptor Peptide

In a second aspect the invention provides a peptide comprising an amino acid sequence having sequence identity to the peptide of SEQ ID NO: 1.

Laminin Receptor Peptide

The inventor has surprisingly discovered that a laminin receptor peptide can be used for the treatment of amyotrophic lateral sclerosis (ALS), Motor Neurone Disease (MND) or Frontotemporal Dementia (FTD). This is thought to occur through a reduction in plasma glucagon levels, which are high in amyotrophic lateral sclerosis (ALS), Motor Neurone Disease (MND) and Frontotemporal Dementia (FTD) patients. Since this property of the laminin receptor peptide was not previously known, the present invention encompasses a peptide having sequence identity to SEQ ID NO: 1.

In one embodiment, the peptide according to the present invention may comprise an amino acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or more sequence identity to SEQ ID NO: 1. Within these embodiments, sequence identity may be assessed by any means. However, sequence identity is preferably assessed using the Smith-Waterman algorithm.

In one embodiment, the peptide according to the present invention may comprise the amino acid sequence of SEQ ID NO: 1. In certain embodiments the peptide according to the present invention may not comprise any additional amino acids which form part of a contiguous sequence of amino acids found in the sequence of the laminin receptor (SEQ ID NO: 6) other than SEQ ID NO: 1.

In another embodiment, the peptide may consist of the amino acid sequence of SEQ ID NO: 1.

Any post-translational modification of the peptide according to the present invention is contemplated. For example, the peptide may be glycosylated, phosphorylated, acetylated or methylated at one or more amino acids.

Peptide Multimer

In one embodiment, the peptide according to the present invention may be a peptide multimer comprising two or more peptide molecules. Herein, the terms "laminin receptor peptide molecule", "laminin receptor peptide", "peptide molecule" and "peptide" will be used interchangeably to refer to a peptide having any of the forms described above.

In one embodiment, the laminin receptor peptide multimer according to the present invention may comprise two, three, four, five, six, seven, eight, nine, ten or more laminin receptor peptide molecules. Preferably, the laminin receptor peptide multimer is a laminin receptor peptide dimer, i.e. comprises two laminin receptor peptide molecules.

In certain embodiments the two or more peptide molecules within the peptide multimer may or may not be identical.

Preferably, the two or more peptide molecules within the peptide multimer each comprise or consist of the sequence of SEQ ID NO: 1.

The point of attachment between the two or more peptide molecules within the peptide multimer may be located at any position within the two or more peptide molecules. In certain embodiments the point of attachment may or may not be located at the same position within each peptide molecule. In certain embodiments the two or more peptide molecules may be attached through their termini. In a preferred embodiment in which the peptide multimer is a peptide dimer, the two peptide molecules are attached through their amino-termini.

Within the peptide multimer, two peptide molecules may be linked by a disulphide bridge. It is well known within the field of protein biochemistry that a disulphide bridge is formed by reaction between the thiol groups of two cysteine residues, and has the sequence R-S-S-R'. Within an embodiment in which the peptide multimer is a peptide dimer, the two peptide molecules may be attached in any orientation. Preferably the two peptide molecules are attached through their termini and more preferably the two peptide molecules are attached through their amino-termini. In other words, the disulphide bridge is preferably located at the amino-terminus of each peptide molecule.

It will be apparent to the skilled person that the peptide of SEQ ID NO: 1 does not include a cysteine residue required to form a disulphide bridge. Therefore, the invention contemplates the inclusion of an additional cysteine residue within each peptide molecule present within the peptide multimer. The additional cysteine residue may be located at any position within each peptide molecule and the additional cysteine residue may or may not be located at the same position within each peptide molecule. Preferably, the additional cysteine residue is located at either the amino-terminus or the carboxy-terminus of each peptide molecule. For example, all peptide molecules may have an additional cysteine residue located at their amino-terminus, all peptide molecules may have an additional cysteine residue located at their carboxy-terminus, or one or more peptide molecules may have an additional cysteine residue located at its amino-terminus and one or more peptide molecules may have an additional cysteine residue located at its carboxy-terminus. Preferably, the multimer is a dimer and both peptide molecules have an additional cysteine residue located at their amino-terminus.

Preferably the additional cysteine residue is present within each peptide molecule immediately adjacent to the sequence of SEQ ID NO: 1. However, the inclusions of additional amino acids (e.g. 1, 2, 3, 4, 5 or more additional amino acids) between the sequence of SEQ ID NO: 1 and the additional cysteine residue is also contemplated.

Herein, a peptide comprising the sequence of SEQ ID NO: 1 and an additional cysteine residue is contemplated. The additional cysteine residue is preferably located at the amino-terminus of SEQ ID NO: 1. In one embodiment the invention encompasses a peptide comprising the amino acid sequence of SEQ ID NO: 2. In certain embodiments the peptide may not comprise any additional amino acids which form part of a contiguous sequence of amino acids found in the sequence of the laminin receptor (SEQ ID NO: 6) other than SEQ ID NO: 1. In another embodiment the peptide may consist of the sequence of SEQ ID NO: 2.

In a preferred embodiment, the peptide multimer is a peptide dimer. In a further preferred embodiment, the laminin receptor peptide dimer according to the present invention comprises two peptide molecules comprising or consisting of SEQ ID NO: 2, which may be linked by a disulphide bridge between the two cysteine residues.

In a preferred embodiment, the peptide multimer is a peptide dimer. In a further preferred embodiment, the laminin receptor peptide dimer according to the present invention comprises the sequence of SEQ ID NO: 3. In a more preferred embodiment, the peptide dimer according to the present invention consists of the sequence of SEQ ID NO: 3.

In certain embodiments the peptide multimer according to the present invention may not comprise any additional amino acids which form part of a contiguous sequence of amino acids found in the sequence of the laminin receptor (SEQ ID NO: 6) other than SEQ ID NO: 1.

Fusion Proteins

In one embodiment the invention provides a fusion protein comprising the peptide or peptide multimer of the invention.

The fusion protein may comprise one or more functional domains in addition to the peptide or peptide multimer of the invention. For example, the fusion protein may comprise one or more tags, biotin molecules, purification handles or effector domains.

Herein, the fusion protein preferably does not comprise a contiguous sequence of amino acids found in the laminin receptor (SEQ ID NO: 6) other than SEQ ID NO: 1.

Nucleic Acid

In one embodiment the invention provides a nucleic acid encoding the peptide, peptide multimer or fusion protein of the invention. The nucleic acid may be DNA or RNA.

The nucleic acid according to the present invention may comprise a nucleic acid sequence having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or more sequence identity to SEQ ID NO: 4 or SEQ ID NO: 5. Within these embodiments, sequence identity may be assessed by any means. However, sequence identity is preferably assessed using the Smith-Waterman algorithm.

In a preferred embodiment, the nucleic acid may comprise SEQ ID NO: 4 or SEQ ID NO: 5. Preferably, the nucleic acid does not comprise a contiguous sequence of nucleotides found in the laminin receptor (SEQ ID NO: 7) other than SEQ ID NO: 4.

In a more preferred embodiment, the nucleic acid may consist of SEQ ID NO: 4 or SEQ ID NO: 5.

Vectors

In one embodiment the invention provides a vector comprising the nucleic acid of the invention. The vector may be any vector suitable for the recombinant production of a protein or peptide encoded by the nucleic acid within the vector. For example, the vector may be a yeast, virus, plasmid, cosmid or artificial chromosome.

Composition

The invention encompasses a composition comprising the peptide, peptide multimer or fusion protein of the invention and, optionally, a pharmaceutically acceptable excipient.

In one embodiment the invention also provides a syringe comprising the composition of the invention. Herein the composition is preferably intended and suitable for subcutaneous or intramuscular administration.

The inventor contemplates the peptide, peptide multimer, peptide dimer, fusion protein or composition for use in therapy. Further, the inventor contemplates the peptide, peptide multimer, peptide dimer, fusion protein or composition for use in a method of treating amyotrophic lateral sclerosis (ALS), Motor Neurone Disease (MND) or Frontotemporal Dementia (FTD).

The invention will be further understood with reference to the following non-limiting experimental examples.

EXAMPLES

Example 1—Effect of Peptide a on Glucagon Levels

The method of the invention is demonstrated in vitro using isolated pancreatic islet cells and measuring glucagon secretion levels in the presence and absence of the Peptide A dimer (SEQ ID NO: 3).

It has previously been demonstrated that disruption of lipid rafts on α-cells by cholesterol depletion resulted in disorganization of signalling molecules and enhanced glucagon release (Xia et al. Endocrinology, 2007, 148:2157-2167). Digestion of pancreatic tissue with collagenase to isolate islets causes similar disruption to the signalling molecules via disorganization of ECM components including laminin, fibronectin and collagen (Lee & Blaufox, J Nucl Med, 1985, 25:72-76) that results in similarly abnormally high glucagon secretion. Surprisingly, the inventor has demonstrated that the addition of the Peptide A dimer (SEQ ID NO: 3) to collagenase treated isolated pancreatic islet cultures can normalize glucagon secretion compared to control cultures, as shown in Table 1, below.

Islets from 2 Wistar rats (~250 g) were isolated according to the method of Li et al. (Nature Protocols, 2009, 4:1649-1652) and suspended in 30 ml RPMI 1640 containing 11 mmol/L glucose and 10% FCS. One ml islet suspension was added to each well of 24-well plates. Peptide A dimer (SEQ ID NO: 3) was dissolved in HBSS at 100 μg/ml and added to wells at a final concentration of 1 μg/ml. After appropriate incubation times, samples were removed for glucagon measurements using Quantikine ELISA Immunoassay (R&D Systems).

TABLE 1

Glucagon levels secreted from isolated rat islet cultures in culture medium alone compared to cultures in presence of Peptide A dimer of this invention

| Time (hours) | Glucagon level (pg/ml) | | % Reduction | P value |
|---|---|---|---|---|
| | Medium alone | Medium plus Peptide A | | |
| 4 | 622.2 +/− 7.7 | 425.6 +/− 14.8 | 31.6% | P = 0.0163 |
| 24 | 252.5 +/− 8.9 | 144.8 +/− 8.8 | 44.8% | p < 0.0001 |
| 72 | 218.9 +/− 2.9 | 98.3 +/− 4.7 | 55.2% | P = 0.0011 |

Glucagon secretion in vitro from isolated pancreatic islets in RPMI 1640 medium containing 11 mmol/L glucose is demonstrated to be higher than expected from experimental evidence of in vivo glucagon secretion and blood volume of an average rat (Ruiter et al., Diabetes, 2003, 52: 1709-1715 & Wang et al., J Histochem Cytochem. 1999, 47:499-506). The higher in vitro levels of glucagon secretion are due to collagenase induced ECM disruption as stated above. In test cultures containing the Peptide A dimer (SEQ ID NO: 3), glucagon secretion was reduced by 31.6% within 4 hours of incubation. Further samples taken at 24 and 72 hours of incubation demonstrated 44.8% and 55.2% reduction in glucagon secretion respectively reaching normality, compared to the control cultures without the Peptide A dimer.

The blood volume of a 250 g rat can be estimated to be ~15 ml according to the formula of Lee & Blaufox (J Nucl Med, 1985, 25:72-76). Therefore, glucagon secretion from islets isolated from two Wistar rats suspended in a volume of 30 ml and dispensed in 1 ml aliquots should be representative of in vivo plasma glucagon concentrations in the average rat. Reported figures of mean glucagon concentrations in Wistar rats during light hours and dark hours varied from a mean of 80.1+/−3.5 pg/ml to 87.3+/−3.4 pg/ml; in fasted rats the concentrations increased to a peak of 102 pg/ml (Wang et al., J Histochem Cytochem. 1999, 47:499-506). It can be seen in Table 1 that 4 hours after culture of freshly isolated rat islets, the glucagon concentration of 622.2 pg/ml is ~6-fold higher than the peak in vivo level measured in the rat. This is due to the degradation and loss of ECM components in freshly isolated islets, which occurs immediately after enzymatic digestion and affects the organization of the signalling molecules in the lipid rafts of α-cells.

The reconstitution of the ECM explains the gradual decline of the pathologically elevated secreted glucagon levels towards normality over the 3-day culture period shown in Table 1. At each time point, the Peptide A dimer ameliorated the glucagon levels until by 72 hours (day three), addition of the Peptide to the cultures resulted in normal levels of glucagon secretion (98.3 pg/ml, Table 1) comparable to the expected in vivo levels of about 80 to 102 pg/ml as reported by Ruiter et al. (Diabetes, 2003, 52: 1709-1715). This demonstrates that the Peptide of this invention is capable of restorative bridging of lipid raft scaffolding and reorganization of numerous signal transduction pathways residing in lipid rafts.

Example 2—Clinical Data

Clinical data were obtained from 19 ALS/MND patients treated on a named patient basis, for a period of 6 months, with the Peptide A dimer (SEQ ID NO: 3).

Average time from diagnosis to treatment was 17.8 months and the decline rate from diagnosis to start of treatment was established for each patient, which averaged at −1.24+/−0.7 decline per month on the ALSFRS-R score. Mean ALSFRS-R score at start of treatment was 32.94+/−8.13, median score 36 (min-max 15-44). Summary data are shown in Tables 2 and 3, below.

TABLE 2

ALSFRS-R scores from 19 ALS/MND patients obtained at start of treatment (A Baseline), predicted score based on decline rate from score at diagnosis to start of treatment (B Predicted) and actual ALSFRS-R score to time of analysis (C Actual)

| Time Point | ALSFRS-R Score | Predicted Decline | Actual Decline | % Slower Progression |
|---|---|---|---|---|
| A Baseline | 32.94 +/− 8.13 | A-B = 8.99 | A-C = 3.41 | 62.07% |
| B Predicted | 23.95 +/− 11.24 | P = 0.0001 | | |
| C Actual | 29.53 +/− 8.26 | | P = 0.0001 | |

Table 2, above, shows 62% slower progression of disease in a group of patients that reflect the general ALS/MND population many of who would not normally be eligible for inclusion in clinical trials due to the severity of their condition. Furthermore, a subgroup of these patients with a faster predicted decline than the average of the group, showed a slower progression on treatment (76.6%, Table 3 below) than the whole group (62.07%, Table 2). Included in this group of 19 patients are 2 participants who stabilized and rose one point each on the ALSFRS-R scale. This is considered to be a rare occurrence estimated at 1% or less. In this treatment group 2/19 is 10.5% of the group.

TABLE 3

ALSFRS-R scores from 7 of 19 ALS/MND patients obtained at start of treatment (A Baseline), predicted score based on decline rate from score at diagnosis to start of treatment (B Predicted) and actual ALSFRs-R score to time of analysis (C Actual)

| Time Point | ALSFRS-R Score | Predicted Decline | Actual Decline | % Slower Progression |
|---|---|---|---|---|
| A Baseline | 30.43 +/− 9.98 | A-B = 14.7 | A-C = 3.43 | 76.6% |
| B Predicted | 15.71 +/− 11.44 | P = 0.005 | | |
| C Actual | 27.00 +/− 9.90 | | P = 0.033 | |

The only FDA approved drug Riluzole for ALS/MND (Bensimon G et al., N. Engl. J. Med. 1994, 330: 585-591) has been shown to have 2-3 months survival advantage which was significant in the group of patients with bulbar onset and showed a positive trend in those with limb onset. There was no functional advantage demonstrated. Edaravone, a free radical scavenger currently approved in Japan, failed to show efficacy during a 24 week treatment period in an initial Phase III trial (Abe et al., Amyotrophic Lateral Sclerosis and Frontotemporal Degeneration, 2014, 15: 610-617). However, on identifying a subgroup of mildly symptomatic participants whose decline seemed to slow down on Edaravone, a second Phase III trial was performed in a selected mildly symptomatic group. Over 24 weeks, those on Edaravone lost 5 points on the ALSFRS-R score while the placebo group lost 7.5 points. This represents a slowing down of progression of 33.3% in this mildly symptomatic subgroup.

The data collected using Peptide A of this invention compare very favourably with currently available treatments including Riluzole and Edaravone, especially considering that patients of a wide severity range were included in the study with an ALSFRS-R mean score at study start of 32.9 (min-max 15-44) (see Table 2). The first Phase III trial of Edaravone failed to show any efficacy even in a less severely affected mixed patient population with a median ALSFRS-R score of 43 (min-max 31-48). A recently published Phase II trial of a novel immune modulator of inflammatory monocyte/macrophages (NP001) in ALS/MND patients with a mean baseline ALSFRS-R of 38, also failed to demonstrate a significant slowing of decline of the ALSFRS-R score (Miller et al., Neurol Neuroimmunol Neuroinflamm, 2015; 2; DOI 10.1212/NXI. 000).

REFERENCES

Abe K, Itoyama Y, Sobue G, Tsuji S, Aoki M et al. Confirmatory double-blind, parallel-group, placebo-controlled study of efficacy and safety of edaravone (MCI-186) in amyotrophic lateral sclerosis patients. Amyotrophic Lateral Sclerosis and Frontotemporal Degeneration 2014; 15: 610-617.

Bensimon G et al. A controlled trial of riluzole in amyotrophic lateral sclerosis. ALS/Riluzole Study Group. N. Engl. J. Med. 1994; 330: 585-591.

Blin O, Desnuelle C, Guelton C, Aubrespy G et al. Anomaly in the neurotransmitter amino acids in amyotrophic lateral sclerosis: a therapeutic application. Rev. Neurol (Paris). 1991; 147: 392-394.

Cabrera O, Jacques-Silva M C, Speier s, Yang S-N et al. Glutamate is a positive autocrine signal for glucagon release. Cell Metab. 2008; 7: 545-554.

Charlton M R, Nair K S. Role of hyperglucagonemia in catabolism associated with type 1 diabetes: effects on leucine metabolism and resting metabolic rate. Diabetes 1998; 47: 1748-1756.

Doge J C, Treleaven C M, Fidler J A, Tamsett T J, Bao C, Searles M, et al. Metabolic signatures of amyotrophic lateral sclerosis reveal insights into disease pathogenesis. PNAS 2013; 110:10812-10817.

Hubbard R W, Will A D, Peterson G W, Sanchez A, Gillian W W, Tan S A. Elevated plasma glucagon in amyotrophic lateral sclerosis. Neurology 1992; 4:1532-1534.

Hyashi M, Yamada H, Uehara S, Marimoto R et al. Secretory granule-mediated co-secretion of L-glutamate and glucagon triggers glutamatergic signal transmission in Islets of Langerhans. J Biol Chem. 2003; 278: 1966-1974.

Iwasaki Y, Ikeda K, Kinoshita M. Plasma amino acid levels in patients with amyotrophic lateral sclerosis. J Neurol Sci. 1992; 107: 219-222.

Jovanovic K, Chetty C J, Khumalo T, Dias B D et al. Novel patented therapeutic approaches targeting the 37/67 kDa laminin receptor for treatment of cancer and Alzheimer's disease. Expert Opin. Ther. Patents, 2015; 25:567-582.

Lee H B and Blaufox M D. Blood volume in the rat. J Nucl Med, 1985; 25:72-76

Li D-S, Yuan Y-H, Tu H-J, et al. A protocol for islet isolation from mouse pancreas. Nature Protocols 2009; 4:1649-1652.

Miller R G, Block G, Katz J S, Barohn R J et al. Randomized phase 2 trial of NP001, a novel immune regulator: Safety and early efficacy in ALS. Neurol Neuroimmunol Neuroinflamm 2015; 2; DOI 10.1212/NXI. 000.

Ness G C, Chambers C M. Feedback and hormonal regulation of hepatic 3-hydroxy-3-methylglutaryl coenzyme A reductas: the concept of cholesterol buffering capacity. Proc Soc Exp Biol Med 2000; 224: 8-19.

Ngo S T, Steyn F J, Huang L, Mantovani S, Pfluger C M M, Woodruff, T M et al. Altered xpression of metabolic proteins and adipokines in patients with amyotrophic lateral sclerosis. Journal of the Neurological Sciences. 2015; 357: 22-27.

Preedy V R, Garlick P J. The effect of glucagon administration on protein synthesis in skeletal muscles, heart and liver in vivo. Biochem J 1985; 15: 575-581.

Ruiter M, La Fleur S E, van Heijningen C, et al. The daily rhythm in plasma glucagon concentrations in the rat is modulated by the biological clock and by feeding behavior. Diabetes. 2003; 52: 1709-1715.

Wang R N, Paraskevas S, Rosenberg L. Characterisation of integrin expression in islets isolated from hamster, canine, porcine and human pancreas. J Histochem Cytochem. 1999; 47:499-506.

Xia F, Leung Y M, Caisano G et al. Targeting of Voltage-gated K+ and Ca2+ channels and Soluble N-ethylmaleimide-sensitive factor attachment protein receptor proteins to cholesterol-rich lipid rafts in pancreatic α-cells: Effects on glucagon secretion stimulus-coupling. Endocrinology 2007; 148:2157-2167.

```
                       Sequence listing (Peptide A amino acid sequence)
                                              SEQ ID NO: 1
VPSVPIQQFPTEDWS (Peptide A amino acid sequence with additional
N-terminal cysteine)
                                              SEQ ID NO: 2
CVPSVPIQQFPTEDWS (Peptide A dimer amino acid sequence)
                                              SEQ ID NO: 3
CVPSVPIQQFPTEDWS

CVPSVPIQQFPTEDWS (Peptide A nucleotide sequence)
                                              SEQ ID NO: 4
GTGCCCAGCGTGCCCATCCAGCAGTTCCCCACCGAGGACTGGAGC (Peptide A nucleotide sequence with additional
N-terminal cysteine)
                                              SEQ ID NO: 5
TGCGTGCCCAGCGTGCCCATCCAGCAGTTCCCCACCGAGGACTGGAGC (Laminin receptor amino acid sequence)
                                              SEQ ID NO: 6
MSGALDVLQMKEEDVLKFLAAGTHLGGTNLDFQMEQYIYKRKSDGIYIIN

LKRTWEKLLLAARAIVAIENPADVSVISSRNTGQRAVLKFAAATGATPIA

GRFTPGTFTNQIQAAFREPRLLVVTDPRADHQPLTEASYVNLPTIALCNT

DSPLRYVDIAIPCNNKGAHSVGLMWWMLAREVLRMRGTISREHPWEVMPD

LYFYRDPEEIEKEEQAAAEKAVTKEEFQGEWTAPAPEFTATQPEVADWSE

GVQVPSVPIQQFPTEDWSAQPATEDWSAAPTAQATEWVGATTDWS (Laminin receptor nucleotide sequence)
                                              SEQ ID NO: 7
ATGAGCGGCGCCCTGGACGTGCTGCAGATGAAGGAGGAGGACGTGCTGAA

GTTCCTGGCCGCCGGCACCCACCTGGGCGGCACCAACCTGGACTTCCAGA

TGGAGCAGTACATCTACAAGAGGAAGAGCGACGGCATCTACATCATCAAC

CTGAAGAGGACCTGGGAGAAGCTGCTGCTGGCCGCCAGGGCCATCGTGGC

CATCGAGAACCCCGCCGACGTGAGCGTGATCAGCAGCAGGAACACCGGCC
```

```
AGAGGGCCGTGCTGAAGTTCGCCGCCGCCACCGGCGCCACCCCCATCGCC

GGCAGGTTCACCCCCGGCACCTTCACCAACCAGATCCAGGCCGCCTTCAG

GGAGCCCAGGCTGCTGGTGGTGACCGACCCCAGGGCCGACCACCAGCCCC

TGACCGAGGCCAGCTACGTGAACCTGCCCACCATCGCCCTGTGCAACACC

GACAGCCCCCTGAGGTACGTGGACATCGCCATCCCCTGCAACAACAAGGG

CGCCCACAGCGTGGGCCTGATGTGGTGGATGCTGGCCAGGGAGGTGCTGA

GGATGAGGGGCACCATCAGCAGGGAGCACCCCTGGGAGGTGATGCCCGAC

CTGTACTTCTACAGGGACCCCGAGGAGATCGAGAAGGAGGAGCAGGCCGC

CGCCGAGAAGGCCGTGACCAAGGAGGAGTTCCAGGGCGAGTGGACCGCCC

CCGCCCCCGAGTTCACCGCCACCCAGCCCGAGGTGGCCGACTGGAGCGAG

GGCGTGCAGGTGCCCAGCGTGCCCATCCAGCAGTTCCCCACCGAGGACTG

GAGCGCCCAGCCCGCCACCGAGGACTGGAGCGCCGCCCCCACCGCCCAGG

CCACCGAGTGGGTGGGCGCCACCACCGACTGGAGC
```

The invention claimed is:

1. A peptide multimer comprising two or more peptide molecules, wherein:
   (a) each of the two or more peptide molecules comprise the amino acid sequence of SEQ ID NO: 1; or
   (b) each of the two or more peptide molecules comprise an amino acid sequence having at least 80% identity to the sequence of SEQ ID NO: 1;
   and wherein the peptide multimer does not comprise a contiguous sequence of amino acids found in the laminin receptor (SEQ ID NO: 6) other than SEQ ID NO: 1.

2. A fusion protein comprising the peptide multimer of claim 1.

3. A composition comprising the peptide multimer of claim 1 and a pharmaceutically acceptable excipient.

4. A syringe comprising the composition of claim 3.

5. The peptide multimer of claim 1, wherein the peptide multimer comprises the sequence of SEQ ID NO: 3.

6. The peptide multimer of claim 5, wherein the peptide multimer consists of the sequence of SEQ ID NO: 3.

7. The peptide multimer of claim 1, wherein the peptide multimer is a peptide dimer comprising two peptide molecules, wherein:
   (a) each of the two peptide molecules comprise the amino acid sequence of SEQ ID NO: 1; or
   (b) each of the two peptide molecules comprise an amino acid sequence having at least 80% identity to the sequence of SEQ ID NO: 1.

8. The peptide dimer of claim 7, wherein the two peptide molecules are linked by a disulphide bridge.

9. The peptide dimer of claim 8, wherein the disulphide bridge is located at the amino-terminus of each peptide molecule.

10. A nucleic acid encoding the peptide of claim 1.

11. A vector comprising the nucleic acid of claim 10.

12. A peptide comprising the amino acid sequence of SEQ ID NO: 2.

13. The peptide of claim 12, wherein the peptide consists of the sequence of SEQ ID NO: 2.

14. A peptide dimer comprising two peptide molecules of claim 12.

15. The peptide dimer of claim 14, wherein the two peptide molecules are linked through a disulphide bridge formed from the amino-terminal cysteine residue of each peptide molecule.

* * * * *